United States Patent [19]

Mark et al.

[11] 4,247,484

[45] Jan. 27, 1981

[54] KETO-DIPHENOL COMPOUNDS

[75] Inventors: Victor Mark, Evansville; Charles V. Hedges, Mt. Vernon, both of Ind.

[73] Assignee: General Electric Company, Pittsfield, Mass.

[21] Appl. No.: 76,974

[22] Filed: Sep. 20, 1979

[51] Int. Cl.³ .................. C07C 49/22; C07C 49/237; C07C 49/252
[52] U.S. Cl. .................................... 568/326; 568/329
[58] Field of Search .................. 260/590 C, 590 FA; 568/72

[56] References Cited

U.S. PATENT DOCUMENTS

| | | | |
|---|---|---|---|
| 2,069,573 | 2/1937 | Bolton | 568/721 |
| 2,883,365 | 4/1959 | Mathas | 568/721 |
| 3,936,493 | 2/1976 | Karmas | 260/590 C |
| 4,133,821 | 1/1979 | West et al. | 260/590 C |

*Primary Examiner*—James H. Reamer
*Attorney, Agent, or Firm*—William F. Mufatti

[57] ABSTRACT

Novel keto-diphenol compounds are disclosed. These compounds are intermediates in the production of novel tetraphenolic compounds which have utility as branching agents in the production of novel, randomly branched polycarbonates.

5 Claims, No Drawings

KETO-DIPHENOL COMPOUNDS

This invention relates to novel keto-diphenol compounds that are intermediates in the production of novel tetraphenolic branching agents.

BACKGROUND OF THE INVENTION

Polycarbonates are well known, commercially important materials which are produced in large quantities. Such polymers are typically prepared by reacting a carbonate precursor with a dihydric phenol to provide a linear polymer consisting of units of the dihydric phenol linked to one another through carbonate linkages. These polymers have outstanding mechanical, thermal, and optical properties such as high tensile strength, optical clarity (transparency), thermal and dimensional stability and impact strength.

These aromatic polycarbonates differ from most thermoplastic polymers in their melt rheology behavior. Most thermoplastic polymers exhibit non-Newtonian flow characteristics over essentially all melt processing conditions. Newtonian flow is defined as the type of flow occurring in a liquid system where the rate of shear is directly proportional to the shearing force. However, in contrast to most thermoplastic polymers, polycabonates prepared from dihydric phenols exhibit Newtonian flow at normal processing temperatures and shear rates below 300 reciprocal seconds.

Two other chararacteristics of molten thermoplastic polymers are considered to be significant for molding operations: melt elasticity and melt strength. Melt elasticity is the recovery of the elastic energy stored within the melt from distortion or orientation of the molecules by shearing stresses. Melt strength may be simply described as the tenacity of a molten strand and indicates the ability of the melt to support a stress. Both of these characteristics are important in extrusion blow molding, particularly in fabrication by extrusion blow molding. Non-Newtonian flow characteristics tend to impart melt elasticity and melt strength to polymers thus allowing their use in blow molding fabrication. In the usual blow molding operation, a tube of a molten thermoplastic is extruded vertically downward into a mold, followed by the introduction of a gas, such as air, into the tube thus forcing the molten plastic to conform to the shape of the mold. The length of the tube and the quantity of material forming the tube are limiting factors in determining the size and wall thickness of the objects that can be molded by this process. The fluidity of the melt obtained from bisphenol-A polycarbonate, or the lack of melt strength as well as the paucity of extrudate swelling, serve to limit blow molding applications to relatively small, thin walled parts. Temperatures must generally be carefully controlled to prevent the extruded tube from falling away before it attains the desired length and the mold is closed around it for blowing. Consequently, the Newtonian behavior of polycarbonate resin melts has severely restricted their use in the production of large hollow bodies by conventional extrusion blow molding operations as well as the production of various other shapes by profile extrusion methods.

Thermoplastic randomly branched polycarbonates exibit unique properties of non-Newtonian flow, melt elasticity and melt strength which permit them to be used to obtain such articles as bottles which were not heretofore easily or readily produced with linear polycarbonates. Therefore, there is a need for branching agents that will promote and facilitate the formation of thermoplastic randomly branched polycarbonates.

DESCRIPTION OF THE INVENTION

The novel compounds of the present invention are keto-diphenol compounds of the formula I:

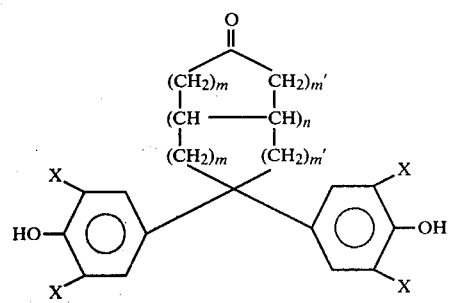

wherein each X substituent is independently selected from phenyl, H, Cl, Br, and $C_1$–$C_5$ alkyl; each m and m' are integers which are independently selected from 0, 1, 2 and 3; and n is an integer of either 0 or 1, with the proviso that the sum of all the m and m' integers and n is at least 2, and with the further proviso that, if n is 0, at least one of the m integers is greater than 0 and at least one of the m' integers is greater than 0.

In the specification and claims, the terms $C_1$–$C_5$ represent radicals having from 1 to 5 carbon atoms. The term "alkyl" is used herein to represent both straight and branched chain alkyl groups.

The invention's novel keto-diphenol compounds have been found to have utility in the production of novel tetraphenolic branching agents. These branching agents are utilized in the production of randomly branched aromatic polycarbonates when copolymerized with dihydric phenols in simple, one-step processes.

These novel keto-diphenol compounds are obtained from the corresponding dione precursors and monofunctional phenols under either acid or alkaline condensing conditions, as shown by the following generalized equation and as illustrated by the detailed procedures described in the examples:

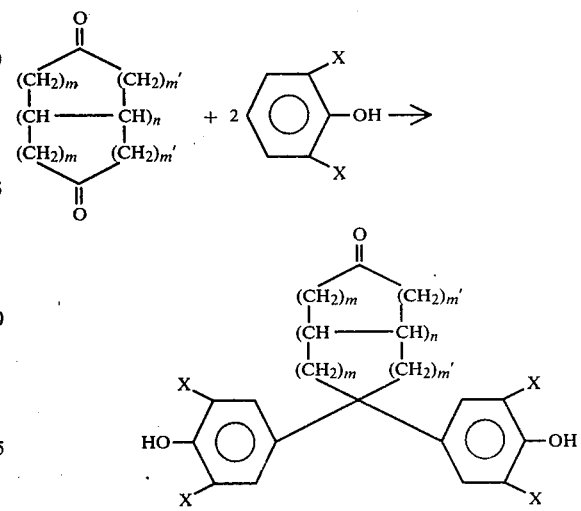

wherein the symbols X, m, m' and n are as set forth above.

In this reaction the molar ratio of the phenol to dione starting materials should be at least 2:1. Molar ratios significantly above 2:1, such as, for example, 10:1 or more, may be utilized without deleterious side affects, since the excess phenol also functions as a reaction solvent. When the reaction is carried out under acidic conditions, a catalyst containing the sulfhydryl (-SH) function may be employed. Examples of the sulfhydryl catalysts are ethanethiol, 1-butanethiol, thiophenol and mercaptoacetic acid.

The condensation reaction is best carried out by utilizing the phenolic reactant in excess of the stoichiometric amount. With phenols that are solid at ambient temperature, this method requires reaction temperatures near or above the melting point of the phenol that is used in excess. In addition, non-phenolic solvents, such as acetic acid, acetic anhydride, methylene chloride, can be used.

The reaction temperature encompasses ambient temperatures to elevated temperatures, such as 100° C. or higher. Although the reaction rate is faster at higher temperatures, there is also an increase in undesired by-products.

The condensation reaction can be carried out either at atmospheric or superatmospheric pressures.

The progress of the condensation reaction can be monitored by chromatographic or spectroscopic methods to follow the production of the invention's keto-diphenol compounds. The thus-formed keto-diphenol compound can be recovered by stripping off the excess phenol and purified by recrystallization, elution chromatography, or other methods known to those skilled in the art. Preferred solvents of recrystallization are methylene chloride, benzene, cyclohexane, methanol, ethanol and alcohol-water mixtures. Elution chromatography is carried out best over alumina or silica, using a variety of solvents as eluants.

It is understood that if the keto-diphenol compound is allowed to remain in the reaction medium, there will be some conversion to the tetraphenolic branching agent of formula II below. If the original molar ratio of the phenol to dione starting materials is greater than 4:1, the conversion to the tetraphenolic compound will be practically complete.

The new keto-diphenols compounds of the present invention can be used for the preparation of the novel tetraphenolic branching agents of formula II below:

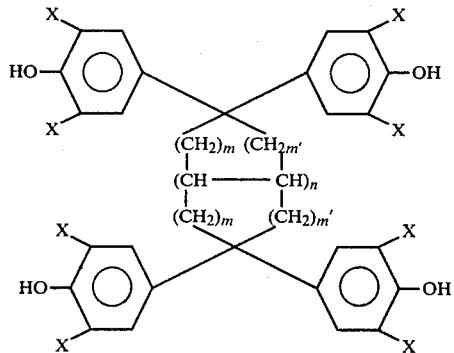

wherein X, m, m' and n are as defined above.

As set forth above, these tetraphenolic compounds will be produced from the invention's intermediate keto-diphenol compounds if the keto-diphenol intermediate remains in the reaction medium.

Alternatively, the keto-diphenol compounds may be purified according to the procedures set forth above, isolated and reacted with a phenol compound of the formula

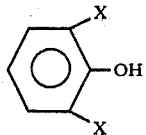

wherein X is as set forth herein.

In this reaction, the molar ratio of the phenol starting material to the keto-diphenol compound must be at least 2:1, with the other reaction conditions similar to those employed for the preparation of the keto-diphenol compounds as set forth above. In this reaction, it is preferred to employ a stoichiometric excess of phenol.

The tetraphenolic compounds, which are prepared from the invention's keto-diphenol compounds, can be used to prepare branched polycarbonate resins according to the methods set forth in our copending application Ser. No. 076,973, filed Sept. 20, 1979, and as exemplified below.

DESCRIPTION OF THE PREFERRED EMBODIMENTS

The following examples are set forth to illustrate the invention and are not to be construed to limit the scope of the invention.

EXAMPLE 1

Preparation of the keto-diphenol: 1,1-bis(4-hydroxyphenyl)-cyclohexan-4-one.

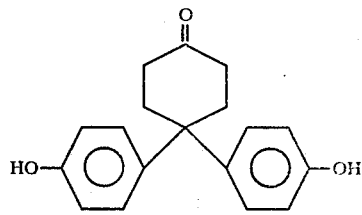

Into a molten mixture of 300 g (3.2 mole) of phenol and 22.42 g (0.2 mole) of 1,4-cyclohexanedione (m.p. 77.0°–78.5° C.), there was introduced hydrochloric acid gas at 50° C. until saturation was obtained. The resulting reaction mixture, that acquired a red color, was kept at 50° C. until the separation of white solids was complete. Gas chromatography confirmed the production of the title compound in the warm filtrate, by its shorter retention time of 23.9 minutes than the tetraphenol, which emerged at 33.3 minutes.

EXAMPLE 2

Preparation of the tetraphenol: 1,1,4,4-tetrakis(4-hydroxyphenyl)cyclohexane.

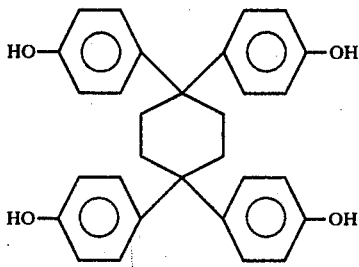

The keto-diphenol produced in Example 1 was allowed to remain in the reaction medium, whereupon it was quantitatively converted into the title tetraphenol, as determined by gas chromatography. The precipitate was filtered off through a sintered glass funnel and the filtercake rinsed with methylene chloride until phenol-free. The colorless crystalline tetraphenol was 99.3% pure by gas chromatographic analysis and had a melting point of 328°-329° C. Stripping of the phenolic mother liquor and the methylene chloride washing yielded more of the above tetraphenol contaminated to a small extent with 1-(2-hydroxyphenyl)-1,4,4-tris(4-hydroxyphenyl)cyclohexane.

EXAMPLE 3

Preparation of a polycarbonate branched with 1,1,4,4,-tetrakis(4-hydroxyphenyl)cyclohexane.

To a well stirred mixture of 2283 g (10 moles) of 2,2-bis-(4-hydroxyphenyl)propane, (BPA), 7000 ml of methylene chloride, 5500 ml of water, 31.1 g (0.33 mole) of phenol, 20.2 g (0.2 mole) of triethylamine and enough 45% aqueous sodium hydroxide solution to maintain a pH of 11.5, there was added a clear, colorless solution of 9.05 g (0.020 mole) of 1,1,4,4-tetrakis (4-hydroxyphenyl)cyclohexane, prepared in accordance with Example 2, in 30% aqueous sodium hydroxide. The introduction of phosgene into the well stirred reaction mixture was carried out at a rate of 30 g/minute for 47 minutes, continuously adjusting the pH to remain between 11.1 and 11.8, until the BPA content of the aqueous phase was reduced to 8 parts per million.

The recovered branched polycarbonate from the washed, neutral methylene chloride phase by steam precipitation and drying had the following properties: intrinsic viscosity 0.619 dl/g; molecular number average 18,300; molecular weight average 40,500; Z-average 71,800; modified melt flow 16,800 csec.; melt index ratio 2.34 and notched Izod impact 16.0 fl.lb.

EXAMPLE 4

Preparation of the keto-diphenol: 1,1-bis(4-hydroxy-3,5-dimethylphenyl)cyclohexan-4-one.

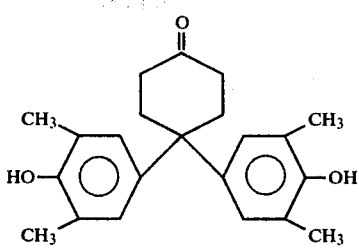

The procedure of Example 1 was repeated, except that 400 g of 2,6-xylenol was substituted for phenol and 1 ml of 1-butanethiol cocatalyst was also added to thereby produce the title compound.

EXAMPLE 5

Preparation of the keto-diphenol: 3,3-bis(4-hydroxyphenyl)-bicyclo [3.3.0]octan-7-one.

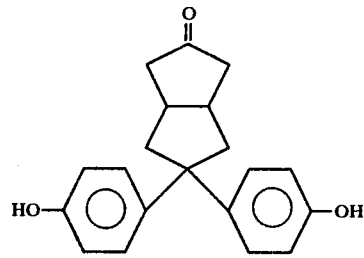

The procedure of Example 1 was repeated, except that cyclohexanedione was replaced with 27.6 g (0.2 mole) of bicyclo [3.3.0]octane-3,7-dione (m.p. 84°-86° C.) to thereby produce the title compound.

EXAMPLE 6

Preparation of the keto-diphenol: 3,3-bis(4-hydroxy-3-methylphenyl)bicyclo[3.3.0]octan-6-one.

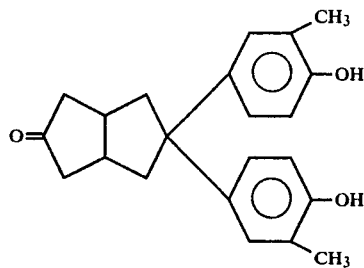

The procedure of Example 1 was repeated except that phenol was replaced with o-cresol, to thereby produce the title compound.

Structurally depicted below are additional examples of novel keto-diphenols which can be prepared by the procedures as generally set forth herein:

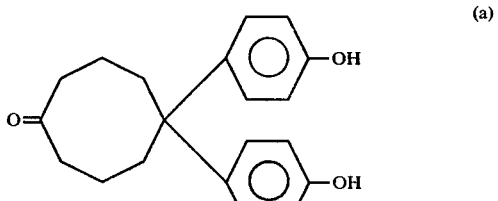

(a)

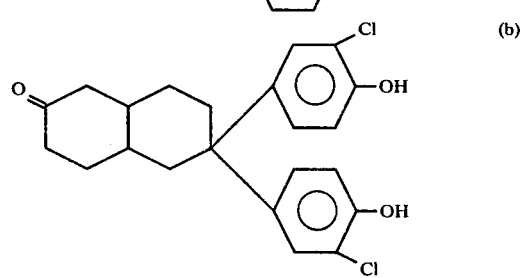

(b)

(c)

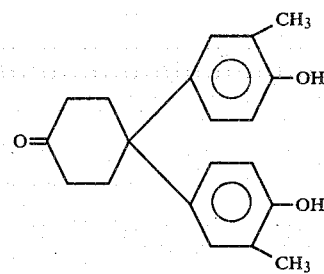

(d)

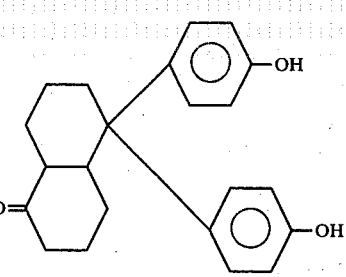

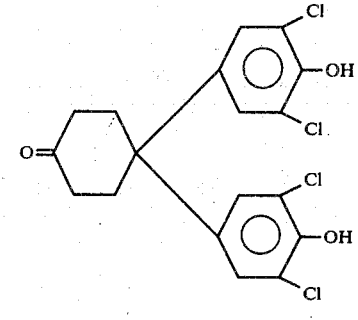

(e)

What is claimed is:

1. A keto-diphenol compound of the formula

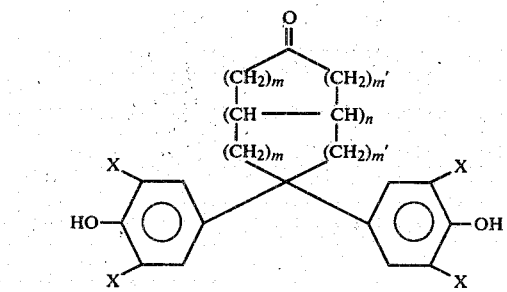

wherein each X substituent is independently selected from phenyl, H, Cl, Br, and $C_1$–$C_5$ alkyl; each m and m' are integers selected independently from 0, 1, 2 and 3; and n is an integer of either 0 or 1, with the proviso that the sum of all the m and m' integers and n is at least 2, and with the further proviso that, if n is 0, at least one of the m integers is greater than 0 and at least one of the m' integers is greater than 0.

2. The compound 1,1-bis(4-hydroxyphenyl)cyclohexene-4-one.

3. The compound 1,1-bis(4-hydroxy-3,5-dimethylphenyl)cyclohexan-4-one.

4. The compound 3,3-bis(4-hydroxyphenyl)bicyclo[3.3.0]octan-7-one.

5. The compound 3,3-bis(4-hydroxy-3-methylphenyl)bicyclo-[3.3.0]octan-7-one.

* * * * *